United States Patent [19]

Shapiro et al.

[11] Patent Number: 5,217,899
[45] Date of Patent: Jun. 8, 1993

[54] CELL STRETCHING APPARATUS

[75] Inventors: Alan R. Shapiro, Sharon; Martha L. Gray, Cambridge; Luis A. Melendez, Norwood; Jonathan L. Schaffer, Newton, all of Mass.; John D. Wright, Sandown, N.H.; Jose G. Venegas, Swampscott, Mass.

[73] Assignees: The General Hospital Corporation, Boston; Massachusetts Institute of Technology, Cambridge, both of Mass.

[21] Appl. No.: 572,683

[22] Filed: Aug. 24, 1990

[51] Int. Cl.⁵ .............................................. C12M 3/00
[52] U.S. Cl. .................................. 435/284; 435/285; 435/316
[58] Field of Search .............. 435/284, 285, 287, 299, 435/296–298, 300, 301, 310, 316

[56] References Cited

U.S. PATENT DOCUMENTS

| | | | |
|---|---|---|---|
| 3,812,016 | 5/1974 | Muller | 195/143 |
| 3,853,712 | 12/1974 | House et al. | 195/127 |
| 4,087,327 | 5/1978 | Feder et al. | 195/1.7 |
| 4,456,683 | 6/1984 | Lintilhac et al. | 435/3 |
| 4,839,280 | 6/1989 | Banes | 435/285 |
| 4,851,354 | 7/1989 | Winston et al. | 435/284 |
| 4,940,853 | 7/1990 | Vandenburgh | 435/1 |

OTHER PUBLICATIONS

"Characterization of The Surface Strain Applied to Cyclically Stretched Cells In Vitro", Gilbert et al, 35th Annual Meeting, Orthopaedic Research Society, Feb. 6–9, 1989, Las Vegas, Nev. (p. 249).
"Think About A Novel Method For Culturing Cells In A Mechanically Active Environment", A brochure of the Flexcell Corp., McKeesport, Pa. 15132 (1–412–66–4–FLEX).
"Introducing the Vitrodyne A New Force In Cell and Tissue Culture", A brochure from Biomechanical Instruments of Burlington, Vt. 05401.

Primary Examiner—Michael G. Wityshyn
Assistant Examiner—William A. Beisner
Attorney, Agent, or Firm—Lahive & Cockfield

[57] ABSTRACT

Disclosed is an apparatus and method for imparting to a living culture of cells biaxial mechanical forces which approximate the mechanical forces to which cells are subjected in vivo. The apparatus includes a displacement applicator which may be actuated to contact and stretch a membrane having a living cell culture mounted thereon. Stretching of the membrane imparts biaxial mechanical forces to the cells. These forces may be uniformly applied to the cells, or they may be selectively non-uniformly applied.

9 Claims, 3 Drawing Sheets

CELL STRETCHING APPARATUS

BACKGROUND OF THE INVENTION

The present invention relates to an apparatus and method for simulating the in vivo mechanical environment to which living cells are subjected. More particularly, the present invention relates to a method and apparatus for imparting biaxial strain to living cells during their growth cycle.

Many living cells, such as those which form tissues including bone, ligament, tendon and muscle are subject to mechanical stress and deformation during the normal course of living. Such a dynamic environment is believed to be important to the growth and health of such cells. Similar mechanical forces which approximate those encountered in vivo are likewise believed to benefit cells grown in a tissue culture. These beneficial mechanical forces include biaxial compression and tension forces applied to the cells during their growth cycle.

The effect of such mechanical influences on cell growth and development is not yet well understood. Consequently, researchers are now investigating the effect of mechanical forces on cells by attempting to approximate, in vitro, the biaxial forces to which cells are subjected in vivo. Thus, in conducting this research it is useful to be able to generate uniform biaxial mechanical forces as well as biaxial forces which have various, predetermined ratios of non-uniformity.

Apparatuses which apply stretching forces to living cells are now known. Typically, these devices include a substrate, upon which cells may be mounted, which itself is adhered to an elastic membrane. When the membrane is stretched through the application of a tensioning force, some of the force is presumably transferred to the individual cells. In reality, however, the stretching forces often are not biaxially applied to the cells, and it is difficult to achieve forces which uniformly affect all of the cells of a given sample. In many cases the cells are subjected only to non-uniform strains. For research and other applications it is important that all cells in the culture experience the same strain.

One apparatus for applying mechanical forces to cells cultures utilizes the application of positive and negative pressure to a membrane upon which the cells are plated. It is generally believed that such pressure-induced deformation of a membrane will not apply a uniform strain to cells mounted upon the membrane at all levels of applied pressure. Moreover, the strain can be difficult to control as it is quite dependent on properties of the membrane. U.S. Pat. No. 4,851,354, however, does claim to achieve a substantially uniform application of biaxial strain to cells grown upon a membrane deformed by the application of pressure. But, Gilbert et al, 35th Annual Meeting, Orthopedic Research Society, p. 249 (Feb. 7, 1989) reports non-uniform strain with a similar pressure mechanism.

Accordingly, there is a need for an apparatus and method for applying to cultures of living cells biaxial forces which simulate an in vivo mechanical environment. It would also be useful to provide such an apparatus which could produce such forces uniformly throughout the cell culture, as well as forces which have selected, non-uniform strain profiles.

It is thus an object of the invention to provide an apparatus able to apply to living cells biaxial forces which approximate those encountered in vivo. It is also an object of the invention to provide such an apparatus which can impart to the cells uniform biaxial forces, as well as selectively non-uniform biaxial forces. A further object of the invention is to provide methods of utilizing such apparatuses to grow living cells in a mechanical environment which approximates that found in vivo. Other objects of the invention will be apparent to those skilled in the art upon review of this disclosure.

SUMMARY OF THE INVENTION

The present invention provides an apparatus which simulates, in vitro, the in vivo mechanical environment to which living cells are exposed by imparting to a cell culture biaxial forces such as compression and tension. The forces imparted to the cell culture by this apparatus can be uniform biaxial forces, or can be of virtually any selected non-uniform force profile.

The apparatus of the invention comprises one or more elastic, biocompatible membranes upon which a cell culture may be deposited. The membrane(s) is securely held in place about the periphery of its area which is to be displaced. A displacement applicator, disposed adjacent one surface (e.g., the bottom surface) of the membrane, is cyclically moved upwardly and downwardly by a force generator such that the applicator directly contacts and deforms the membrane. This membrane deformation imparts biaxial forces (i.e., compression and tension) to the cells mounted thereon. The forces may be uniform in that the strain is substantially the same for all cells in the culture. Alternatively, the strain may be of a selected, non-uniform profile.

As noted above, mechanical deformation is imparted to cells deposited on a pliable membrane by directly contacting the membrane upon which the culture is deposited with a mechanical displacement applicator. It is believed that such a technique for inducing deformation of the membrane best enables the stress/strain profile to be controlled. Uniform biaxial strain may be imparted to the cell culture utilizing a membrane and a displacement applicator which are of corresponding circular shapes. It is important to ensure that the displacement applicator has dimensions only slightly smaller than the dimensions of the membrane, especially where a uniform force profile is desired.

Other shapes of the membrane and displacement applicator, such as ovoid, rectangular and square, may be utilized to yield non-uniform strain profiles. For example, a rectangular shape, with a length to width ratio of 2:1, for the membrane and applicator yield a strain profile where strain along the short axis is twice that along the long axis. By varying the shape and size the membrane and displacement applicator a variety of strain ratios can be achieved.

It is important that friction between the membrane and the force applicator be virtually eliminated, or greatly minimized, to ensure that the desired degree of membrane deformation is achieved to impart either uniform biaxial forces to the cells, or forces of a predetermined non-uniform profile. Thus, the displacement applicator, and the components which it contacts should be made of low friction materials. Lubricants may also be added to the force applicator to further control friction.

The invention also relates to methods of growing cells and simulating an in vivo mechanical environment for the cells using this apparatus.

DETAILED DESCRIPTION OF THE INVENTION

Figure 1:
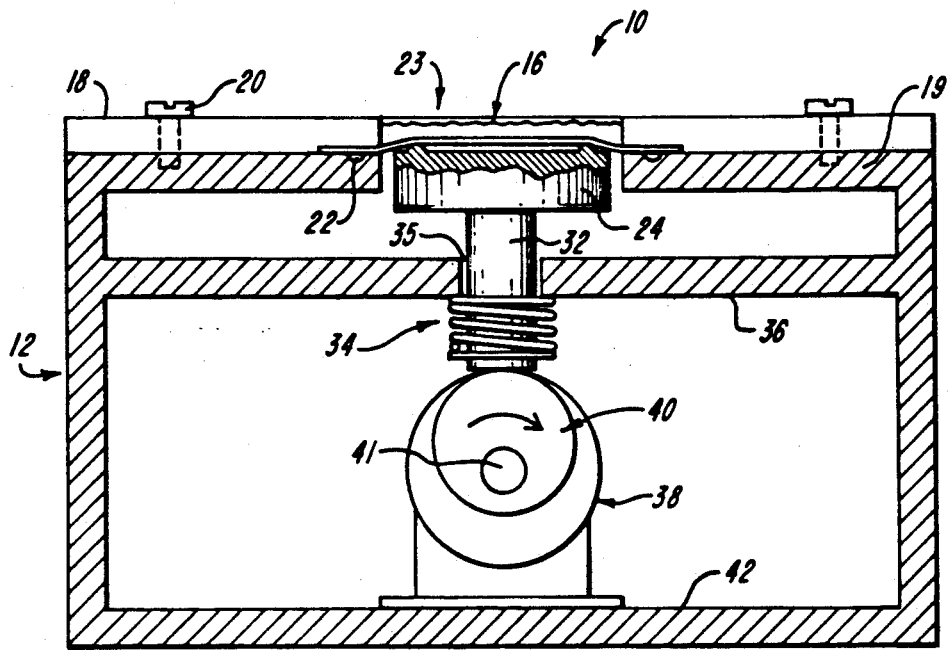
FIG. 1 is a cross-sectional view of the cell stretching apparatus of the present invention.

Referring to FIG. 1, the present invention comprises a cell stretching apparatus 10 which is able to impart to an in vitro cell culture, biaxial mechanical forces which simulate those found in vivo. The apparatus 10 comprises a housing 12 which includes a top plate 18 and mounting screws (or clamps) 20 used to secure an elastic membrane 14, upon which a cell culture 16 is deposited. An upper frame member 19 cooperates with plate 18 and mounting screws 20 to secure the perimeter portions of membrane 14 which are peripheral to the area of the membrane to be stretched. The top plate 18 may also include an aperture or window 23 (or other transparent device) which is disposed directly over the membrane 14 and cell culture. A seal 22, such as an o-ring or similar gasket may be provided to help secure membrane 14 in place and to prevent any leakage of growth medium.

Apparatus 10 also includes a displacement applicator 24 which is disposed below membrane 14. A downwardly projecting rod 32 is secured to the bottom portion of applicator 24. Rod 32 extends through bushing 35 which is formed within intermediate frame member 36. A spring 34, or similar biasing means, may surround the portion of member 32 which extends below bushing 35, to bias the applicator 24 toward a lowered position in which it is out of contact with membrane 14. The spring or biasing means 34 also helps negate any frictional force which may result from the travel of rod 32 within bushing 35.

FIG. 1 further illustrates an embodiment in which an electric motor 38 is mounted to a base plate 42 of housing 12. The motor 38 drives an actuating apparatus 40, such as a cam. Where, for example, the actuating apparatus 40 is a cam, it revolves eccentrically about an axis, contacting the bottom surface of rod 32 and forcing rod 32 and displacement applicator 24 to move upwardly to contact and deform membrane 14. At the end of the upward stroke of rod 32 and applicator 24, cam 40 and spring 34 cooperate to return rod 32 and applicator 24 to a lowered position out of contact with membrane 14. When this occurs the membrane returns to its original, non-deformed position.

The housing 12 of cell stretching apparatus may be constructed of a variety of materials well known to those skilled in the art. Such materials include, but are not limited to, steel, aluminum and plastic.

Membrane 14 may be made of virtually any elastic, biocompatible material. The most preferred materials are those which are low-friction materials and which are elastic up to about 100% strain. Exemplary materials include silicone and thermoplastic elastomers. Other materials well known to those skilled in the art may be used as well.

The shape of the membrane 14 may vary depending upon whether uniform forces are to be applied to the cells mounted on the membrane. When uniform biaxial forces are to be imparted to the cells, a circular membrane should be used. The diameter of such a membrane may be in the range of about 10 mm to 100 mm, and most preferably is about 50 mm to 90 mm in diameter. Other membrane shapes may be used to apply selected non-uniform forces to cells. For example, a rectangular membrane in which the length of the membrane is twice its width, produces a strain ratio of 2:1 for strain along the short axis over strain along the long axis. One skilled in the art will readily appreciate the effect of membrane shape upon the degree of uniformity or non-uniformity of the forces applied to the cells. If a particular strain ratio or profile is desired, one will be able to design a membrane having a shape suitable to produce such a ratio.

The maximum thickness of the membrane depends upon its diameter and elasticity. Preferably, the thickness is less than about 1% of the membrane diameter.

The displacement applicator 24 generally is of a shape which corresponds to that of the membrane 14. Preferably, applicator 24 is of a size which is slightly less than that of the membrane. That is, applicator 24 should be of dimensions as close as possible to the area of membrane 14 which is to be deformed, while allowing the applicator to freely contact the membrane without interference from plates 18 and 19.

Where uniform biaxial forces are to be applied to the cell culture, a circular membrane and a circular displacement applicator should be used. The use of a rectangular membrane and a similarly shaped displacement applicator will result in a non-uniform biaxial strain profile wherein the strain along the short axis of the membrane is greater than that along the long axis of the membrane. Still, all cells will be subjected to consistent and predictable non-uniform biaxial strain. Other membrane shapes, and displacement applicators of a corresponding shape, may be used to yield different non-uniform strain profiles. It is also possible to utilize membranes and displacement applicators which are not of a corresponding shape, in order to produce a variety of other non-uniform force profiles.

The displacement applicator 24 preferably is constructed of very low friction materials such as certain tetrafluoroethylene polymers, acetal polymers, nylon polymers and other low friction polymers and other materials well known to those skilled in the art. Bushing 35 should likewise be constructed of such low friction materials so that rod 32 may travel within bushing 35 with little or no frictional force.

It is important that there be no, or very little, friction between the top surface of displacement applicator 24 and the bottom surface of membrane 14. The absence of any such friction ensures that membrane 14 will deform as desired upon contact with displacement applicator 24 in order to impart a desired uniform or non-uniform biaxial force profile to the cell culture. The use of frictionless or low friction construction materials for the moving parts of apparatus 10 is quite effective in eliminating or minimizing friction. Any existing friction could be eliminated or further reduced by applying a lubricant to the top surface of displacement applicator 24. A variety of lubricants may be used with the present application, and virtually the only requirement of such a lubricant is that it not degrade, penetrate or attack the material from which membrane 14 is made. Exemplary lubricants include silicone materials and hydrogenated vegetable shortening.

Figure 2A:
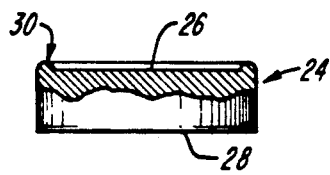
FIG. 2A is a side view of a force applicating disk used in the apparatus of FIG. 1.
Figure 2B:
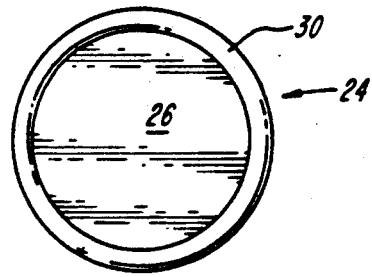
FIG. 2B is a top view of the displacement applicator shown in FIG. 2A.
Figure 3A:
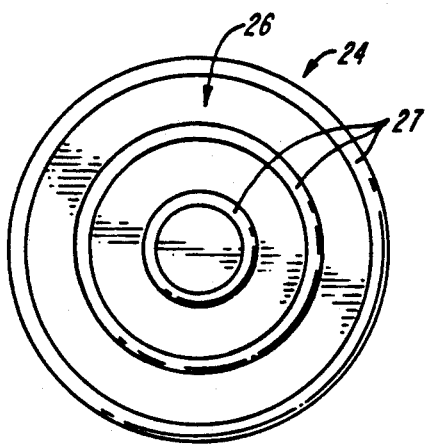
FIGS. 3A and 3B are top views of alternative designs for displacement applicating disks which may be used in the apparatus of FIG. 1.
Figure 3B:
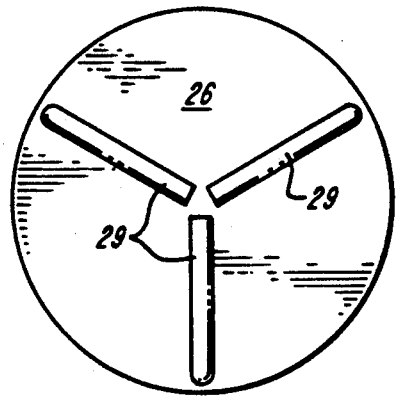

In a preferred embodiment, displacement applicator 24 has an irregular or uneven top surface so that only a relatively small area of the applicator contacts membrane 14 to obviate or minimize any friction between applicator 24 and membrane 14. FIG. 2A and 2B illustrate one embodiment where a circular displacement applicator 24 has a raised ridge 30 which is disposed about the perimeter of the top surface 26 of applicator 24. Preferably, a relatively small hole (not shown) extends through the applicator to permit the passage of air and to avoid ballooning or suction of the membrane surface. FIGS. 3A and 3B illustrate other embodiments of a displacement applicator 24 having different patterns of raised ridge structures on the top surface thereof. As shown in FIG. 3A the raised ridge 27 takes the form of concentric, circular ridges on the top surface 26 of applicator 24. In FIG. 3B, the raised ridge is formed by radial arms 29 which extend outwardly from the center of the applicator. It is understood that a variety of other raised ridge configurations may be used as well. Generally the ridge is raised approximately 0.05 inch to 0.15 inch above the top surface 26 of the displacement applicator 24, and is about 0.125 inch in width.

Figure 4A:
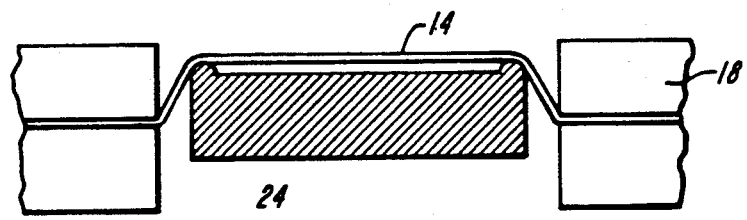
FIGS. 4A and 4B are partial side, sectional views which respectively illustrate the membrane and displacement applicator of FIG. 1 in the deformed and non-deformed condition.
Figure 4B:
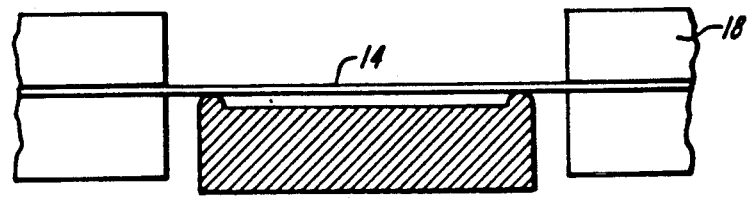

FIGS. 4A and 4B illustrate the operation of the cell stretching apparatus 10. In FIG. 4B, displacement applicator 24 has not yet exerted a force upon membrane 14. In FIG. 4A, membrane 14 has been deformed through application of force by applicator 24. The deformation of the membrane imparts biaxial strain of a desired, non-uniform or uniform profile.

An apparatus similar to that illustrated in FIGS. 4A and 4B, was constructed having a circular, silicone rubber membrane of 0.010 inch in thickness and 3.375 inches in diameter and a displacement applicator 24 of 3.30 inches in diameter. A rectangular grid was drawn on the top surface of the membrane. The grid was made of a plurality of squares, each having dimensions 0.25 inches by 0.25 inches. The displacement applicator was actuated to contact and deform the membrane. At the end of the upward stroke of the displacement applicator, the sizes of the squares making up the grid of the membrane were examined. It was determined that the squares were equally sized, with dimensions of 0.263 inch by 0.263 inch, confirming that the apparatus produced uniform biaxial strain to the top surface of the membrane.

Figure 5:
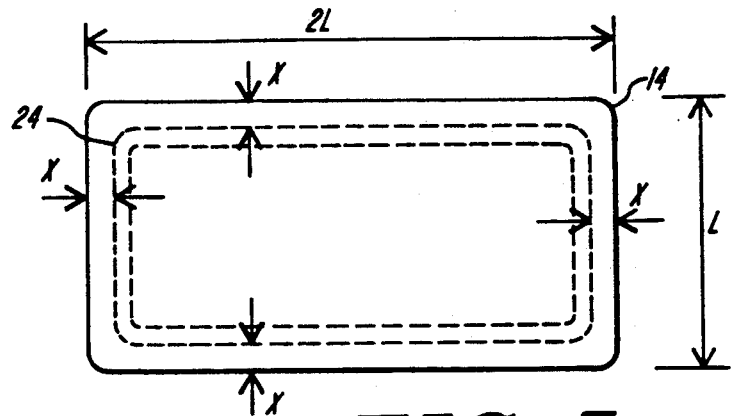
FIG. 5 is a top view of a rectangular elastic membrane and a displacement applicator which may be utilized with the present invention.
Figure 6:
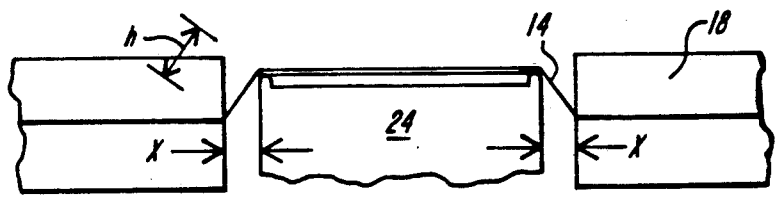
FIG. 6 is partial sectional view of the apparatus of FIG. 5, showing the membrane secured in place in the deformed condition.

FIG. 5 illustrates an embodiment, noted above, where a rectangular membrane and displacement applicator 24 can be utilized to produce different strains on mutually perpendicular axes. The dimensions of the rectangular membrane are 2L by L, while the dimensions of the displacement applicator are 2L-2x by L-2x. FIG. 6 is a cross-sectional view of the apparatus shown in FIG. 5, illustrating membrane 14 in a deformed condition, being stressed by displacement applicator 24. While in the stressed condition the length and width of membrane 14 on each side is increased by $\Delta x = h - x$, for total increase of $2\Delta x$. Thus, strain along the long axis is given by the relationship $$2\Delta x/2L = \Delta x/L$$

Strain along the short axis is given by the relationship $$2\Delta x/L$$

which is twice that along the long axis. By varying the dimensions of the membrane and displacement applicator, as well as the shapes thereof, a variety of strain ratios can be achieved. It is noted, however, that the above analysis neglects strain at the membrane edges which tends to be complex and indeterminate, but which represents a small, negligible percentage of the total membrane area.

Figure 7:
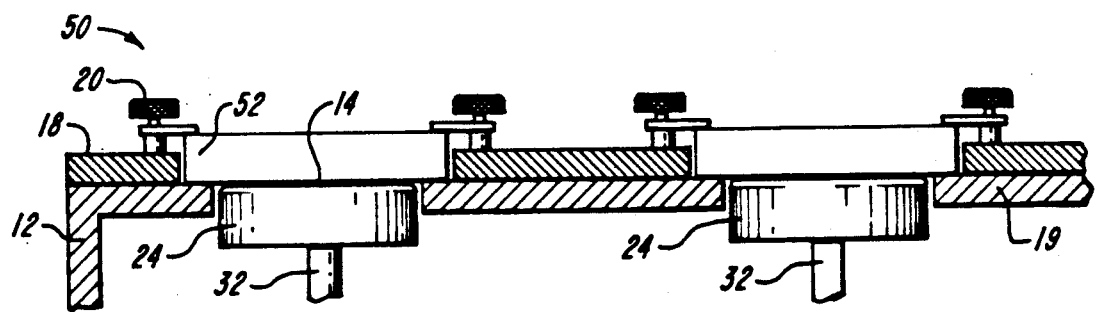
FIG. 7 is a cross-sectional view of an alternative cell stretching apparatus which includes a plurality of individual cell culture-containing units.

FIG. 7 illustrates another embodiment of the invention in which a cell stretching apparatus 50 simultaneously stretches a plurality of cell cultures. In this embodiment a removable and disposable well 52 is mounted in the appropriate location above each of the available displacement applicators 24. The bottom of the specimen wells 52 rest on plate 19 and are secured in place by clamps 20.

Figure 8B:
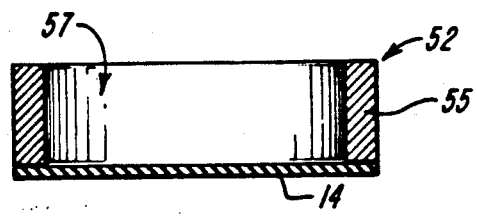
FIG. 8B is a side, sectional view of the apparatus shown in FIG. 8A, along lines 8B—8B.
Figure 8A:
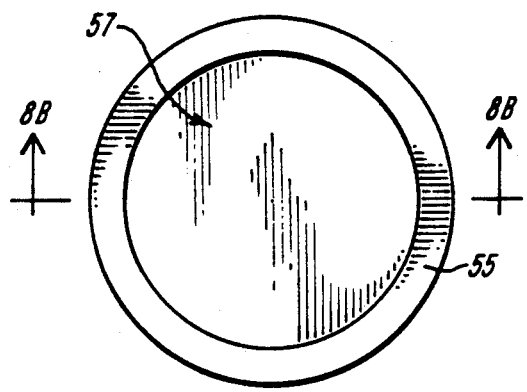
FIG. 8A is a top view of a cell culture-containing unit shown in FIG. 7.

Preferably, the specimen well 52 is constructed of a donut-shaped ring, illustrated in FIGS. 8A and 8B. The ring consists of side walls 55 which define a central aperture 57. A membrane 14 is secured to the bottom of the specimen well 52, such as by adhering edges of the membrane to the bottom surface of the side walls 55 of the specimen well. A top cover (not shown) may or may not be applied to the top surface of the specimen well.

The type and size of the motor used to drive actuator 40 can be readily chosen by one skilled in the art. Electric motors are, however, preferred. In a preferred embodiment the motor drives an actuator, such as a cam. The action of the cam causes the rod 32 and displacement applicator 24 to move up and down. As illustrated in FIG. 1, cam 40 revolves eccentrically about motor shaft 41 resulting in the cyclical upward and downward movement of rod 32 and applicator 24. In an alternative embodiment, not illustrated, the cam may be designed so that the displacement applicator stretches the membrane 14 at rest and moves to create a reduction of stretch (i.e., negative strain or compression).

The cycle of upward and downward movement of applicator 24 depends upon the requirements of a given application and may be varied accordingly by one skilled in the art. Generally, the motor speed may vary between 2 and 80 cycles per minute. However, greater speeds may be used as well.

The percentage of strain of the membrane is determined by the distance traveled by the displacement applicator 24, which in turn is determined by the eccentricity of the cam 40. Therefore, by changing cams one can develop strains of differing amounts. The profile of strain versus time may be varied quite easily simply by changing the cam. For example, one could design cams which gradually increase the strain up to a certain value and maintain that value for a small or large portion of the cycle.

The design of the cell stretching apparatus allows it to be easily placed within an incubator or similar apparatus because electric power may easily be delivered to a motor within the incubator.

The invention may be embodied in other specific forms, not specifically described above, without departing from the spirit and scope thereof.

What is claimed is:

1. An apparatus for applying cyclical mechanical stretching forces to living cells, comprising
   at lest one elastic, biocompatible membrane capable of receiving a culture of living cells and culture medium for said cells, said membrane being suitable for cells to adhere to and grow upon said membrane;
   clamp means for securing the membrane about its entire periphery within the apparatus;
   at least one selectively displaceable applicator means, constructed of a low friction material, for applying a stretching force to said membrane such that the applicator means is a rigid member that applies biaxial strain of the cells growing upon the surface of the membrane, in a uniform or selectively non-uniform profile, said applicator means having a membrane-facing surface with a size slightly less than a shape substantially corresponding to an area of the membrane exposed by the clamp means; and
   force generating means for cyclically moving said applicator means to contact and control displacement of said membrane.

2. The apparatus of claim 1 wherein the membrane-facing surface of the applicator means and the portion of the membrane contacted by the applicator means are circular in shape.

3. The apparatus of claim 2 wherein the membrane-facing surface of said applicator means is irregular and has one or more elevated ridges which contact said membrane.

4. The apparatus of claim 3 wherein at least one raised, membrane contacting ridge is disposed about the perimeter of the membrane-facing surface of the applicator means.

5. The apparatus of claim 4 wherein said ridge is elevated about 0.125 inch above the surface of said applicator means.

6. The apparatus of claim 1 wherein said applicator means further includes a downwardly projecting member attached to a bottom surface of said applicator means.

7. The apparatus of claim 6 wherein said force generating means includes a cam means for contacting said downwardly projecting member to enable the member and the applicator means to move upwardly and downwardly.

8. The apparatus of claim 1 further including a lubricating material applied to the membrane facing surface of said applicator means.

9. The apparatus of claim 1 wherein the clamp means for securing the membrane includes a removable and disposable ring-shaped structure, secured to said apparatus, and having said membrane adhered thereto.

* * * * *